US00PP15169P2

(12) United States Plant Patent
Uchneat

(10) Patent No.: US PP15,169 P2
(45) Date of Patent: Sep. 21, 2004

(54) DOUBLE IMPATIENS PLANT NAMED 'BALPIXDOBUR'

(50) Latin Name: *Impatiens walleriana*
Varietal Denomination: Balpixdobur

(75) Inventor: Michael Uchneat, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 14 days.

(21) Appl. No.: 10/736,729

(22) Filed: Dec. 16, 2003

(51) Int. Cl.[7] ..... A01H 5/00
(52) U.S. Cl. ..... Plt./317
(58) Field of Search ..... Plt./317

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct cultivar of Double Impatiens plant named 'Balpixdobur', characterized by its small, fully double purple/white bicolor flowers, dark green-colored foliage, compact upright and mounded growth habit and excellent basal branching.

1 Drawing Sheet

Latin name of the genus and species of plant claimed: *Impatiens walleriana.*
Variety denomination: 'Balpixdobur'.

BACKGROUND OF THE INVENTION

The present invention relates to a new and distinct cultivar of Double Impatiens plant botanically known as *Impatiens walleriana* and hereinafter referred to by the cultivar name 'Balpixdobur'.

The new cultivar was developed by the inventor in a controlled breeding program during December 2000 at Elburn, Ill. The objective of the breeding program was to develop new Impatiens cultivars with numerous small, fully double flowers, excellent basal branching and upright compact growth habit.

The female (seed) parent of 'Balpixdobur' was the proprietary *Impatiens walleriana* selection designated '3177-1-1-1' (not patented) characterized by its compact growth habit, small single salmon-colored flowers and dark green-colored foliage. The male (pollen) parent of 'Balpixdobur' was the proprietary *Impatiens walleriana* selection '3325-1' (not patented) characterized by its vigorous upright habit, small semi-double burgundy and white bicolor flowers and dark green-colored foliage. 'Balpixdobur' was discovered and selected as one flowering plant within the progeny of the stated cross-pollination in September 2001 and was initially designated '7787-1'.

Asexual reproduction of the new cultivar by terminal stem cuttings in Elburn, Ill. and West Chicago, Ill., has demonstrated that the characteristics of the new cultivar as herein described, reproduce true to type and are firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however any change in phenotype.

It was repeatedly found that the cultivar of the present invention:

It was found that the cultivar of the present invention:

1. Exhibits small, fully double purple/white bicolor flowers,
2. Forms dark green-colored foliage,
3. Exhibits a good basal branching character, and
4. Exhibits a compact, upright and mounded growth habit.

Plants of the new cultivar differ from plants of the female parent primarily in flower type and color and from plants of the male parent primarily in growth habit.

Of the many commercially available Double Impatiens cultivars known to the inventor, 'Balpixdobur' is most similar to 'Sparkler Rose' (U.S. Plant Pat. No. 9,603). However, in side-by-side comparisons conducted in West Chicago, Ill., plants of the new cultivar differed from plants of 'Sparkler Rose' in the following characteristics:

1. Plants of 'Balpixdobur' have smaller flowers than plants of 'Sparkler Rose', and
2. The flowers of 'Balpixdobur' are darker and more purple in color than the flowers of 'Sparkler Rose'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors in 'Balpixdobur'. The plants were grown for 8 weeks in a greenhouse at West Chicago, Ill.

DETAILED DESCRIPTION

Figure 1:
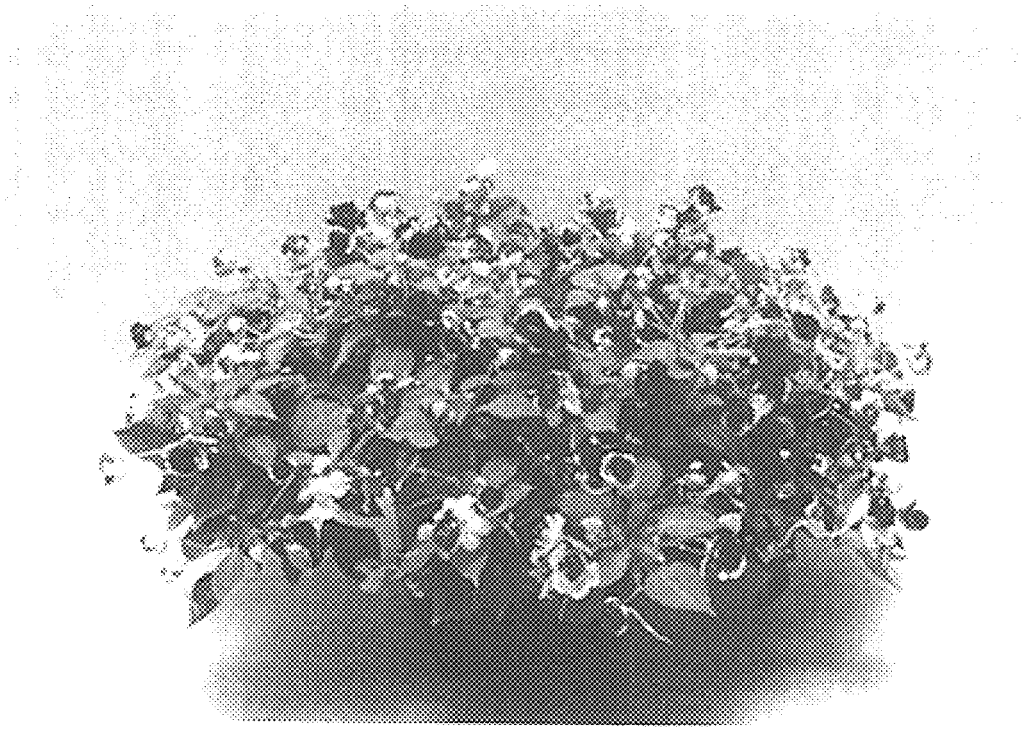
FIG. 1 illustrates a side view of the overall growth and flowering habit of 'Balpixdobur'.
Figure 2:
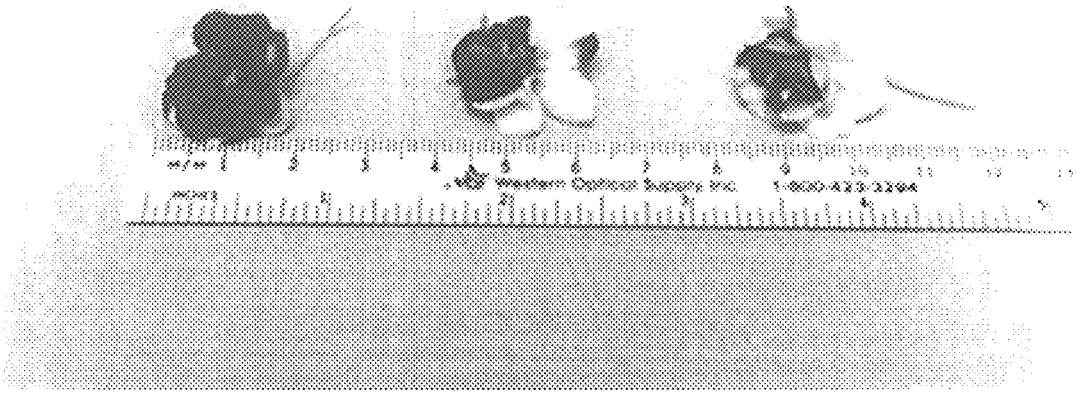
FIG. 2 illustrates a close up view of three flowers, showing the variation of flower color exhibited by 'Balpixdobur'.

The chart used in the identification of colors described herein is The R.H.S. Colour Chart of The Royal Horticultural Society, London, England, 1995 edition, except where general color terms of ordinary significance are used. The color values were determined on Aug. 8, 2003 between 10:00 and 11:45 a.m. under natural daylight conditions.

The following measurements and comparisons describe plants produced from cuttings taken from stock plants and grown under greenhouse conditions comparable to those used in commercial practice. Plants were grown in 10 cm pots for 8 weeks while utilizing a soilless growth medium. Greenhouse temperatures were maintained at approximately 65°–75° F. during the day and approximately 55°–62° F. during the night. Greenhouse light levels of approximately 4,000–6,000 footcandles were maintained during the day.

Botanical classification: *Impatiens walleriana* cultivar 'Balpixdobur'.

Parentage:

*Female (seed) parent.*—Proprietary *Impatiens walleriana* selection designated '3177-1-1-1' (not patented).

*Male (pollen) parent.*—Proprietary *Impatiens walleriana* selection designated '3325-1' (not patented).

Propagation:

*Type cutting.*—Terminal stem.

*Time to initiate roots.*—Approximately 7–14 days with the shorter times generally being experienced in the summer and the longer times in the winter.

*Time to develop roots.*—Approximately 21 days.

*Root description.*—Fine, fibrous.

*Rooting habit.*—Freely branching.

Plant description:

*Habit of growth.*—Compact with good basal branching. A mature plant, 8 weeks after the planting of a rooted cutting, commonly measures approximately 21.6 cm in height and approximately 33.4 cm in width (plant spread).

*Plant form.*—Upright and mounded.

*Lateral branches.*—Quantity: Approximately 3 per plant. Length: Approximately 18 cm. Diameter: Approximately 9 mm. Texture: Glabrous. Color: 146C. Internode length: Approximately 1.6 cm.

*Foliage.*—Type: Simple. Arrangement: Alternate. Shape: Ovate. Apex: Cuspidate/Acuminate. Base: Attenuate. Margin: Crenate/ciliate. Texture: Glabrous. Venation pattern: Pinnate, arcuate. Size of mature foliage: Length: Approximately 3.9 cm. Width: Approximately 2.1 cm. Color of young and mature foliage: Upper surface is closest to 137A, with veins and mid-vein of 145B. Lower surface is slightly lighter than 147B with veins and mid-vein of 145B. Petiole length: Approximately 1.1 cm. Petiole diameter: 2 mm. Petiole texture of both surfaces: Glabrous. Petiole color of both surfaces: 145B.

Flowering description:

*Flowering habit.*—Freely flowering.

*Natural flowering season.*—Year round in greenhouse environment. Flowering is continuous from spring until fall in the garden.

*Lastingness of individual bloom.*—Approximately 5–7 days.

*Quantity of flowers.*—Approximately 15 flowers and 8 buds per stem at any one time.

*Flower buds rate of opening.*—Generally it takes 7–10 days for buds to progress from first color to fully open flowers.

*Mature flower buds (just before opening).*—Shape: Ovoid. Length: Approximately 1.1 cm. Diameter: Approximately 8 mm. Color of petals: 69D with varying amounts of 71C.

*Flower description.*—Type: Fully double. Shape: Round. Diameter: Approximately 2.9 cm. Depth: Approximately 1.3 cm. Borne: Above foliage arising from leaf axils and facing upward or outward. Flowers are not persistent or fragrant.

*Petals.*—Arrangement: Imbricate. Number per flower: Approximately 23. Shape: Obovate. Margin: Entire. Apex: Obtuse. Base: Attenuate. Texture: Glabrous. Appearance: Iridescent. Outermost petals: Length: 1.4 cm. Width: 21.1 cm. Innermost petals: Length: 8 mm. Width: 6 mm.

*Flower color.*—Upper surface of fully opened petals: Background closest to 61B with varying amounts of N155B. Lower surface of fully opened petals: 68B with varying amounts of N155B. Petal color fading with age to: N79B.

*Calyx.*—Quantity of sepals: Three per flower with lower sepal modified into a spur. Sepal apex: Acuminate. Sepal texture: Glabrous. Lateral sepal length: Approximately 3 mm. Lateral sepal width: Approximately 1 mm. Lateral sepal, color of both surfaces: 150C. Lower sepal length: Approximately 1 cm. Lower sepal width: Approximately 8 mm. Lower sepal, color of both surfaces: 150D with tip of 150C.

*Spur.*—Quantity: One per flower. Length: Approximately 3.6 cm. Diameter at base: Approximately 2 mm. Diameter at tip: Approximately 1 mm. Color: Closest to 145C.

*Peduncles.*—Length: Approximately 1.5 cm. Diameter: Approximately 1 mm. Texture: Glabrous. Strength: Strong. Angle to stem: Acute. Color: 145A.

*Reproductive organs.*—None observed.

Seed and fruit development: Neither seed nor fruit production has been observed.

Disease and pest resistance: Resistance to pathogens and pests common to impatiens has not been observed.

What is claimed is:

1. A new and distinct cultivar of Double Impatiens plant named 'Balpixdobur' substantially as herein shown and described, which:

1. Exhibits small, fully double purple/white bicolor flowers,
2. Forms dark green-colored foliage,
3. Exhibits a good basal branching character, and
4. Exhibits a compact upright and mounded growth habit.

* * * * *